United States Patent [19]

Burke et al.

[11] Patent Number: 5,188,456
[45] Date of Patent: Feb. 23, 1993

[54] APPARATUS FOR THERMOMECHANICAL TESTING OF FIBERS

[75] Inventors: Richard A. Burke; James R. Goodall, both of Charlotte; Michael D. Melton, Mooresville; Roy S. Osborne, Charlotte, all of N.C.; Carl D. Patterson, Rock Hill, S.C.

[73] Assignee: Hoechst Celanese Corporation, Somerville, N.J.

[21] Appl. No.: 800,292

[22] Filed: Nov. 29, 1991

[51] Int. Cl.$^5$ ................................ H01N 3/18
[52] U.S. Cl. ........................ 374/50; 73/826; 73/160
[58] Field of Search ............ 73/49, 55, 51, 826, 73/828, 808, 160; 374/46, 14, 50, 49

[56] References Cited

U.S. PATENT DOCUMENTS

| | | | |
|---|---|---|---|
| 3,369,390 | 2/1968 | Chu et al. | 374/52 |
| 3,813,919 | 6/1974 | Taniguchi et al. | 374/50 |
| 4,335,615 | 6/1982 | Kalfa et al. | 73/826 X |
| 4,562,743 | 1/1986 | Bonine | 73/828 |
| 4,841,779 | 6/1989 | Mitsuhashi et al. | 73/826 |
| 4,998,825 | 3/1991 | Hublikar et al. | 374/50 |

Primary Examiner—Daniel M. Yasich
Attorney, Agent, or Firm—Philip P. McCann

[57] ABSTRACT

The invention provides a fiber testing device for thermomechanical testing of fibers which preferably includes a linear step motor coupled to a first fiber gripping jaw. A second fiber gripping jaw is positioned in linear relation to the first gripping jaw and is coupled to a load cell. Advantageously, the apparatus includes a chamber for maintaining a fiber test specimen in a substantially thermally isolated environment during testing of the fiber. A heating means and a cooling means are connected to the chamber. The heating means and cooling means are controlled by a control means which also controls the position of the linear step motor. The fiber testing device of the invention is capable of performing complicated mechanical and thermal fiber testing protocals without operator involvement except for initiation of the testing sequence.

20 Claims, 4 Drawing Sheets 5,188,456

APPARATUS FOR THERMOMECHANICAL TESTING OF FIBERS

FIELD OF THE INVENTION

The invention is directed to an apparatus for testing of fibers to determine various mechanical properties of the fibers. More specifically, the invention is directed to an apparatus for testing fibers which is capable of varying parameters and temperature conditions for fiber testing during separate different tests and/or during a single fiber testing protocol including varied thermal conditions and/or mechanical stress conditions.

BACKGROUND OF THE INVENTION

Testing devices which measure tensile stresses on various materials by stretching and/or compressing these materials are used in numerous industries. Essentially, these devices include various means for mounting of the material to be tested such that the material is attached to the testing device at different portions of the material. The material is then stretched or compressed by the device and, for example, the load during stretching or compression is recorded. Known stress/strain testing instruments of this type are marketed by Instron Corporation.

Stress/strain testing devices are used extensively by fiber manufacturers and fiber end users. By carefully stretching, relaxing or otherwise manipulating fibers under controlled conditions, substantial information relating to fiber strength and expected performance can be determined. For example, measurements can be made on fiber strength such as fiber tenacity which is the force required to break a yarn or filament expressed in grams per denier; fiber elongation including the load exerted by the fiber at a certain specified elongation; fiber shrinkage at various temperatures and the like.

Particularly with industrial fibers which are to be used in various highly demanding environments, such as high temperature environments, it is desirable to measure the response of the fibers to various stress/strain conditions under various thermal conditions. Accordingly, various known testing devices such as devices sold by Instron Corporation can optionally include heating and/or cooled environmental testing chambers for conducting tests on the materials, including fibers.

A testing apparatus for the thermal testing of tire cord is disclosed in U.S. Pat. No. 4,998,825 to Hublikar, et al. This device includes a heating cavity which is constructed to receive a sample of tire cord and wherein heating elements surrounding the cavity are controlled by a computerized temperature recorder. A plurality of weights are used to stress the tire cord under various temperature conditions.

U.S. Pat. No. 4,841,779 to Mitsuhashi, et al. discloses a tension tester which includes a central processing unit for controlling a motor which applies test loads to a specimen. The specimen can be retained within a thermostatic chamber including a cooling coil. Video cameras are used to measure the amount of elongation experienced by a specimen and a load cell measures a tensile load applied to the specimen.

U.S. Pat. No. 4,335,615 to Kalfa, et al. discloses a device for testing materials for stress corrosion cracking in which a pair of rotary stepping motors are used to impart a tensile load to a test sample. The rotary stepping motors are connected via a planetary gear system to the test sample for the application of controlled stress to the sample.

U.S. Pat. No. 3,813,919 to Taniguchi, et al. discloses a testing apparatus for measuring thermal behaviors of filament yarn. This apparatus includes a tube heater which encloses a test specimen. A spiral resistor and air cooling blower are employed for maintaining the specimen at a predetermined temperature. The temperature of the specimen is said to be capable of being increased or decreased rapidly by an electronic temperature controller.

Although these and other known testing apparatus provide the capability for performing various controlled tests on fibers, the known devices can include various drawbacks including the requirement for multiple testing devices in order to perform various different tests. Many of the devices are large and complex. For example, those systems which are highly accurate can typically include gearing systems, mounting systems and the like such that the apparatus can be extremely large. Similarly, with those systems that the test parameters can be varied as chosen by the user of the system, the various parts and portions of the system result in a complete system which is highly complex. Systems are not readily available which are highly accurate, of relatively small size and are capable of varying mechanical testing parameters and temperature conditions during a single test at the option of the user or according to one or more sets of predetermined instructions.

SUMMARY OF THE INVENTION

The invention provides a highly precise and extremely variable fiber testing apparatus. The fiber testing apparatus of the invention can be provided in relatively small size and can be constructed in a relatively simple and straightforward manner while having a minimum of parts. Nevertheless, the fiber testing apparatus of the invention is capable of performing highly sophisticated conventional and unconventional testing protocols on fibers and can provide highly precise and accurate information on fiber properties.

In one aspect, the invention provides a method and apparatus for fiber testing involving the use of linear step motor. The linear step motor includes a forcer arranged for controlled linear movement on a stationary platen. A first fiber gripping means, e.g. a fiber gripping jaw or clamp, is coupled to the forcer of the linear step motor and is arranged for linear motion along a predetermined path in correspondence with the linear motion of the forcer. A second fiber gripping means is positioned at a spaced location and in linear relation to the predetermined linear path of the first fiber gripping means. The second fiber gripping means is coupled to a force measuring means, such as a load cell so that force experienced by the second fiber gripping means is transmitted to the force measuring means. A control means, such as a microcomputer is coupled to the force transmitting means and to the linear step motor and controls the linear motion of the linear step motor according to a set of predetermined instructions.

Because a linear step motor is used to move the first fiber gripping means, no sophisticated gearing system is needed to effect movement of the fiber gripping means or jaw thus simplifying the fiber testing apparatus as compared to conventional fiber testing devices. The linear step motor is additionally, high accurate and can be digitally controlled by the control system, such as a microcomputer so that highly precise tests can be conducted on the fiber and so that highly variable testing protocols as determined by the user or in accordance with standard fiber testing procedures, can be readily conducted on the fibers.

In another aspect of the invention, the invention provides a fiber testing apparatus which includes a chamber arranged for containment of the fiber test specimen and the first and second fiber gripping means during testing of the fiber. A heating means and a cooling means are connected to the chamber for heating and cooling of the chamber. The heating means and cooling means are advantageously capable of rapidly changing the thermal conditions within the chamber and preferably supply a forced stream of heated air or a forced stream of cooled air to the chamber. The heating and cooling means are connected to the control means, such as a microcomputer, so that the temperature conditions within the chamber can rapidly be changed during testing of fibers. A temperature sensor in the chamber is also connected to the control means so that temperature changes effected by the heating means and cooling means can continuously be monitored and so that heating or cooling supplied to the chamber can be varied in response to signals from the temperature sensor. Preferably, the chamber provides a substantially thermally isolated environment for testing of the fiber. Preferably, the means used to mechanically manipulate the fiber within the chamber is a step motor, such as the linear step motor discussed previously.

The testing device of the invention, in its various embodiments can provide numerous advantages and benefits. For example, fibers can be tested during a single testing protocol under a variety predetermined temperature conditions and under a variety of predetermined mechanical conditions so that the strength, elongation, shrinkage and like fiber properties which can change due to exposure of the fiber to various mechanical manipulations and temperature conditions can be measured and predicted. For example, in the tire manufacturing process, fibers in the tire are stretched and heated, then relaxed and heated, then stretched further while heated, and then cooled, while the molding and curing steps in the tire manufacturing process are accomplished. The fiber testing device of this invention can rapidly and readily provide information as to expected changes in fiber elongation and strength according to any given set of heating, stretching, relaxing, cooling and like conditions which the fiber is expected to experience during its incorporation into an end use product, such as a tire. In addition, the fiber testing device of the invention can readily perform conventional fiber test such as tests to determine tenacity, load at specified elongation, elongation at specified load and the like. Moreover, the fiber testing device of the repetitive tests such as the known test for determining work loss, without requiring operator involvement and concomitant operator error.

BRIEF DESCRIPTION OF THE DRAWINGS

In the drawings which form a portion of the original disclosure of the invention.

DETAILED DESCRIPTION OF THE PREFERRED EMBODIMENT

In the following detailed description, there is described a preferred embodiment of the invention for testing of fibers. It will be recognized that although specific terms may be used in describing the perferred embodiment, these are used in the descriptive sense and not generically, and are used for the purposes of description and not of limitation. The invention is susceptible to numerous changes and variations within the spirit and scope of the teachings herein as will be apparent to the skilled artisan.

Figure 1:
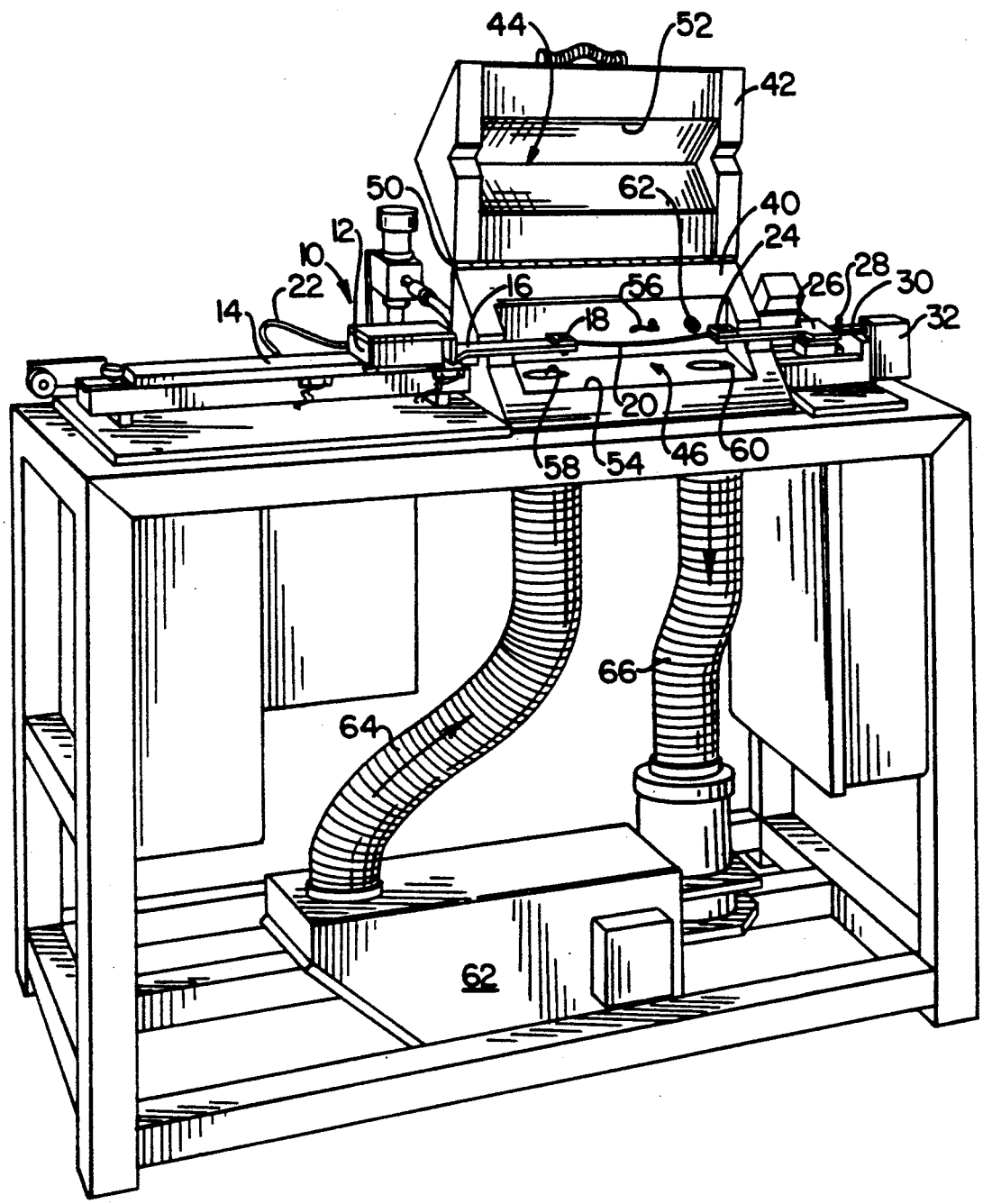
FIG. 1 is a perspective view illustrating a perferred fiber testing device according to the invention.

FIG. 1 illustrates a perspective view of a preferred fiber testing apparatus according to the invention. A linear step motor 10, including a moving forcer 12 and a stationary platen 14, is provided for mechanical fiber manipulation. The movable forcer 12 is connected via a rigid connecting bar 16 to a first fiber gripping jaw 18 which grips the first end of a fiber 20 to be tested. It will be apparent that as forcer 12 is caused to move linearly upon platen 14, the fiber gripping jaw 18 is, in turn, caused to move in a corresponding linear motion along a predetermined linear path as determined by the linear path of forcer 12 upon platen 14. An air hose 22 is attached to the forcer 12 for supply of air to a portion of the forcer 12 which, in turn, provides for an air bearing between the forcer 12 and the platen 14 as discussed in greater detail later.

A second fiber gripping jaw 24 is provided at a location spaced from and in linear relation with the predetermined linear path of the first fiber gripping jaw 18. The second fiber gripping jaw 24 is coupled via a connecting linear bar 26 and a connecting pin 28 to the arm 30 of a conventional load cell 32. It will be apparent that the second fiber gripping jaw 20 is thus positioned at a substantially fixed location while the movement of jaw 18 can provide different degrees of stretching to the fiber 20. The force experienced by the second jaw 24 is then transmitted via bar 26 and arm 30 to load cell 32 for measurement.

A thermally isolated chamber is provided by housing members 40 and 42, each of which define portions 44 and 46 of a cavity for containment of fiber 20 and gripping jaws 18 and 24 when the upper housing member 42 is pivoted downwardly about hinge 50 for mating with the lower housing member 40 thereby providing closure of the cavity formed by the cavity portions 44 and 46. Advantageously, the walls of the housing members 40 and 42 are lined with a relatively thick insulation lining 52 and 54 so that the fiber and fiber gripping jaws are contained within an insulated thermal environment.

A temperature sensor 56 is provided within the interior of the cavity for continuous measurement of the temperature within the cavity. In addition, there is port 58 for admitting forced heated air into the cavity and a port 60 for removing air from the cavity. A port 62 provides cooling air to the cavity via a cooling air "vortex" device which is cooling air device commercially from EXAIR and capable of providing cooling air at a rate of 2000 BTU/Hr.

A heater 62 which includes a fan (not shown) and a heating element (not shown) is provided for supplying heated air to port 58. The heated air is rapidly moved through supply line 64 to port 58 so that the chamber can rapidly be heated. A return line 66 removes heated air via port 60 from the heated chamber. The use of a forced air heating means provides the capability for rapidly changing the temperature within the environmental chamber. For example, using a forced air heater as illustrated in FIG. 1, the temperature within the chamber can be rapidly changed at a rate of up to about 25° C. per minute. Similarly, the use of the vortex cooling apparatus which supplies cooled air via port 62 allows for cooling of the chamber at a rate of up to −60° C. per minute.

Figure 2:
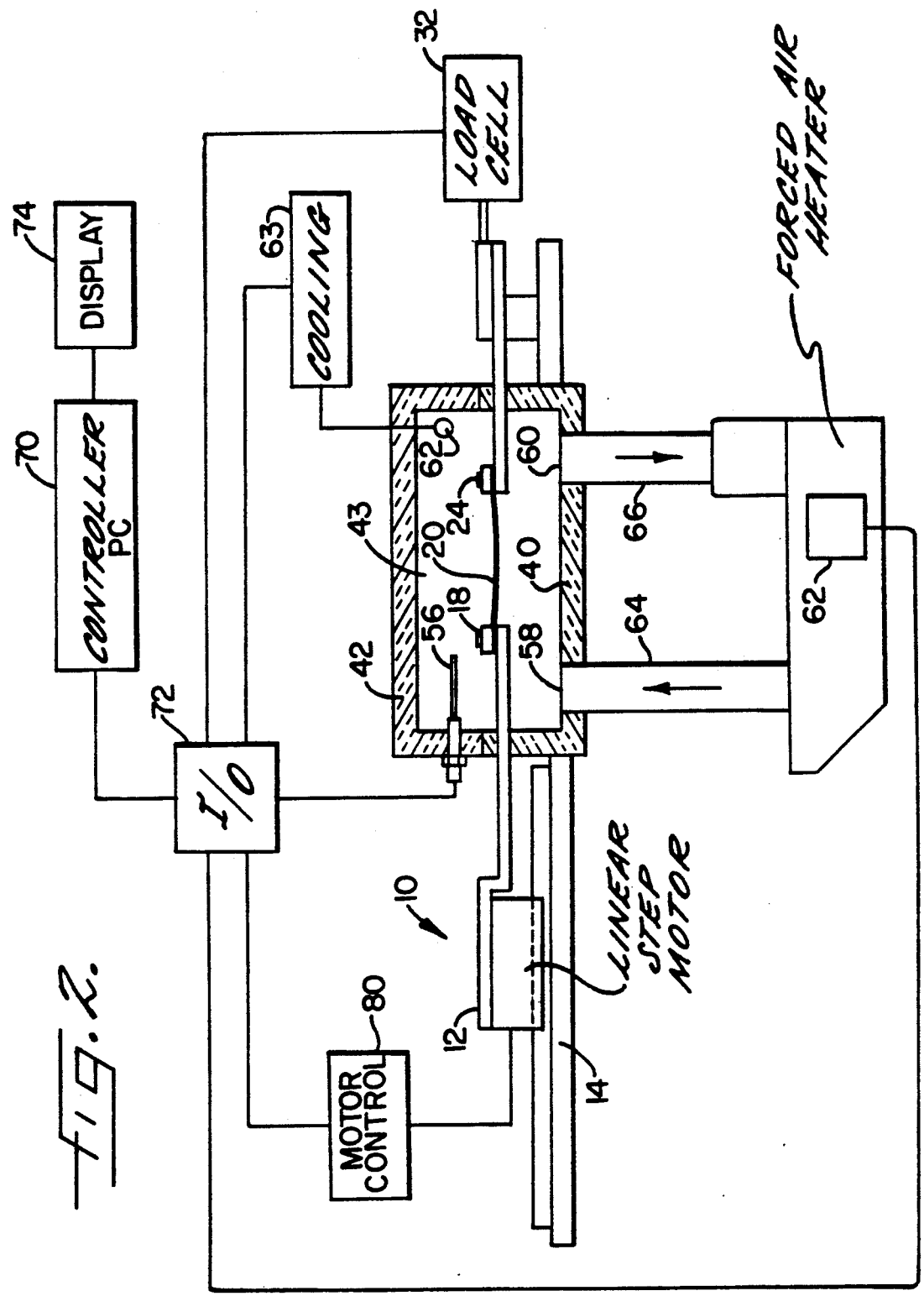
FIG. 2 is a schematic view of a perferred fiber testing device according to the invention.

FIG. 2 schematically illustrates the system for control of the fiber testing apparatus of the invention. As illustrated in FIG. 2 the chamber 43, formed by upper and lower housing members 42 and 44, is shown to be in the closed position. As seen in FIG. 2, a control means 70 which can be a conventional microcomputer or a similar control device is connected via a conventional input/output means 72 to the various parts of the testing apparatus including load cell 32, linear step motor 10, the cooling means 63, the heater 62, and the temperature sensor 56. The controller 70 is typically a digitally operated system and includes a set of predetermined instructions for periodically sampling signals received from load cell 32 and from temperature sensor 56 and for operation of linear step motor 10, cooling means 63 and heating means 62.

Figure 3:
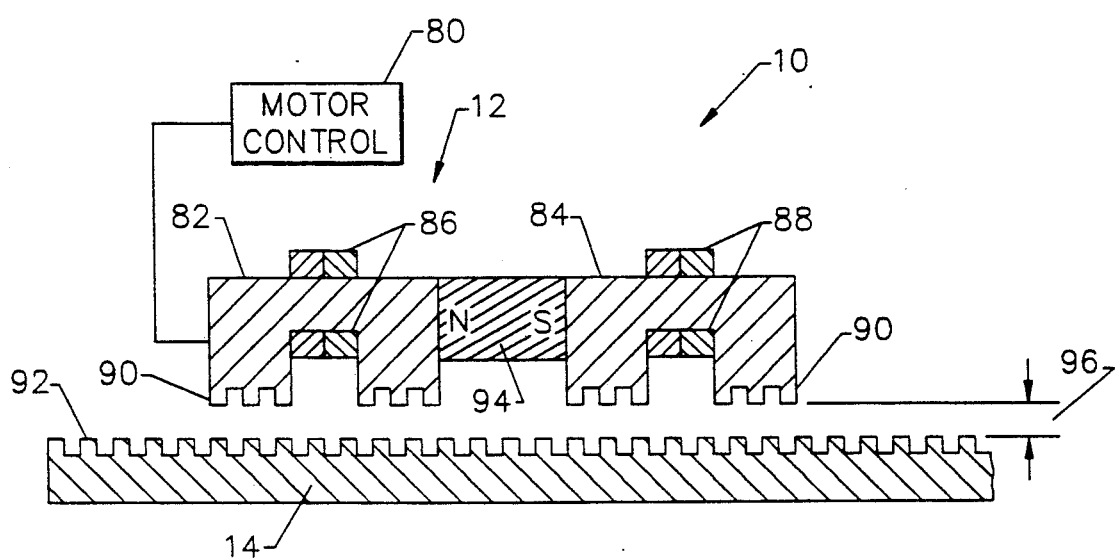
FIG. 3 illustrates a linear step motor which is preferably employed in the testing device of the invention.

A conventional linear step motor 10 is illustrated in FIG. 3. As is known to the skilled artisan, the linear step motor includes a forcer member 12 and a stationary platen member 14. A motor control 80 is typically included as part of the step motor. The forcer includes two electromagnets 82 and 84 including field windings 86 and 88. The two pole faces of each electromagnet are toothed to concentrate the magnetic flux. The teeth 90 on the electromagnet are arranged so that only one set of teeth on each of the electromagnets can be aligned with corresponding platen teeth at a time. A strong rare earth permanent magnet is disposed between the two electromagnets.

Linear stepping motors include bearings between the platen surface and the surface of the electromagnets. The bearings can be mechanical bearings or air bearings. An air bearing operates by floating the forcer on high pressure air introduced through orifices near the pole faces of the forcer. Thus, the forcer is continually disposed a small distance 96 (FIG. 3) above the platen when the air bearing is operational.

The operation of linear step motors is well known. In essence, when current is established in a field winding, the resulting mechanic field tends to reinforce the magnetic flux at one pole face and cancel it at the other. By reversing the current, the reinforcement and cancellation are exchanged. By selectively applying current, it is possible to concentrate flux at any of the forcer's four pole faces. The face receiving the highest flux concentration will attempt to align its teeth with the platen thus moving the forcer in one direction or another.

Linear step motors are known in the art and are available from various sources including PARKER Compumotor Corp. of Rohnert Park, Calif.

Returning to FIG. 2, the linear step motor 10 receives control input from controller 70. In addition, the linear step motor sends position signals via input/output device 72 to controller 70. Position signals sent from the linear step motor 10 to the controller 70 allow for calculation within controller 70 of the exact total amount of movement of the forcer 12 which in turn allows calculation of percent fiber extension or elongation.

Various testing protocols for fibers are well known in the art and can be conducted using the system of the invention. For example, to determine load at specified elongation (LASE) wherein, for example a 5% elongation is specified, the fiber 20 to be tested is first clamped between jaws 18 and 20. Operator input then is used to initiate the test. The controller 70 sends signals to the forcer member 12 for movement in a left direction until the load cell 32 detects an increase in the load on fiber clamping jaw 24. The position of the forcer 12 is then determined by the controller and the forcer 12 is moved further to the left until the position, as calculated by the controller, is reached at which the fiber is elongated 5%. The controller then measures the load on load cell 32 and displays the load via display 74 which can be a video screen and or a printer/plotter.

Figure 4:
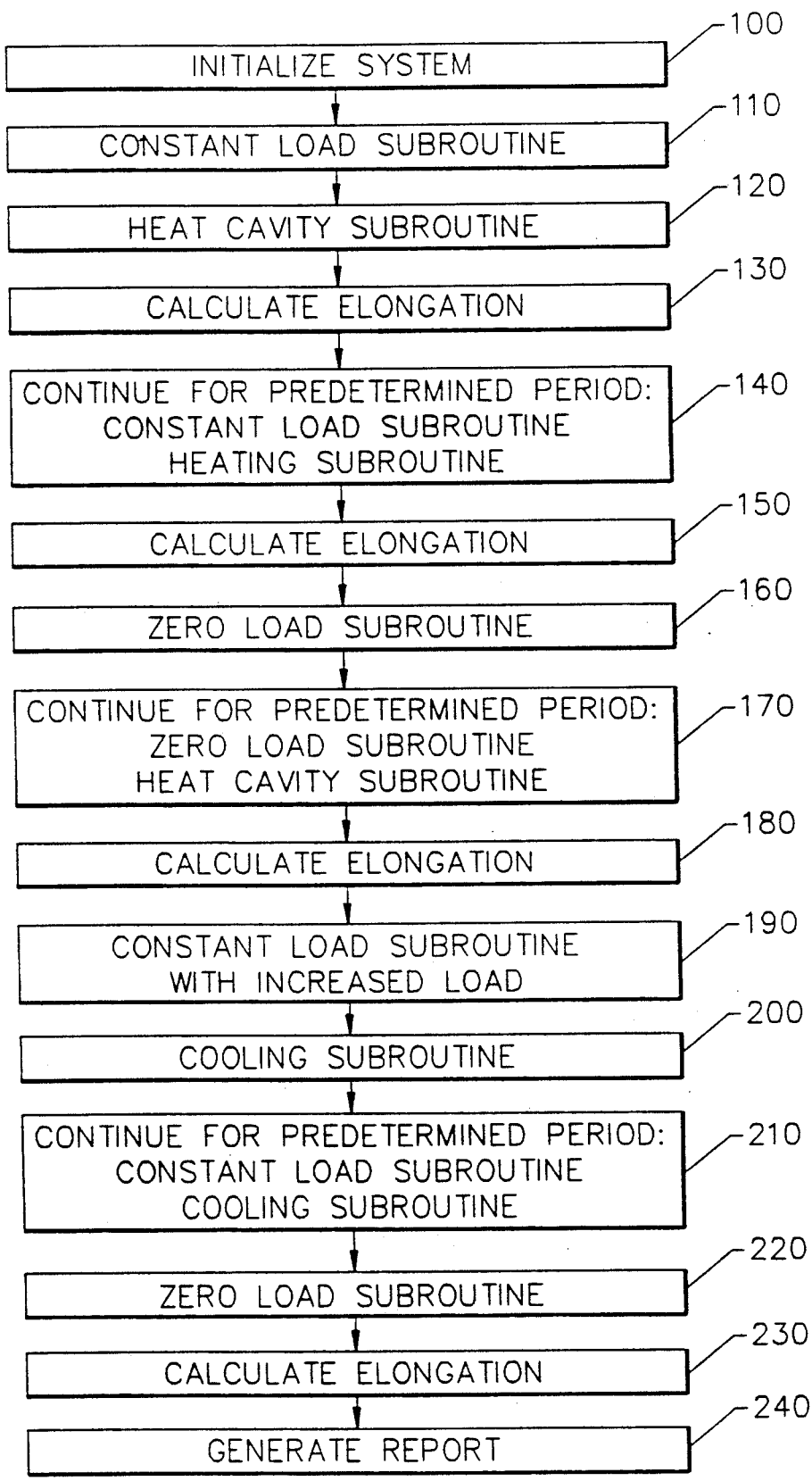
FIG. 4 illustrates a control sequence for performing the Simulated Cure Postcure Inflation Test employing the system of the invention.

FIG. 4 illustrates application of the measuring device of the invention to the industry standard testing protocol known as "simulated cure postcure inflation test". In this test, the fibers are subjected to conditions simulating the conditions which would be experienced by the fibers during a tire manufacturing process. Using prior systems, a testing technician performed certain of the testing steps manually and would spend approximately forty-five minutes conducting the test. With the system of this invention, the test is performed by the testing device. Operator involvement is limited to loading of the fiber in the system and initializing the test.

Referring to FIG. 4, the test is initiated by the operator by loading a fiber sample having a length close to a predetermined amount, e.g. ten inches, into the fiber jaws. The operator then begins the test. In step 100, (FIG. 4) the system is automatically initialized. Initialization of the system by the control means, e.g. the microcomputer, includes the following steps:

determine load cell reading;
move the forcer to the left one discrete step;
measure load on load cell;
move forcer one step to the left; and
repeat load measuring step and forcer moving step until a threshold load is sensed by load cell.

Following the above initializing subroutine, the fiber is assumed to be at zero percent elongation and the control sequence passes to step 110 for the initialization of the constant load subroutine which subjects the fiber to a constant load. This subroutine is conducted by the system as follows:

move forcer to the left;
measure load on load cell;
compare load to predetermined value;
if load is less than predetermined value then return to "move forcer" step;
if load equals predetermined value return to immediately preceding "measure load" step.

The constant load subroutine is continued until the predetermined load on the fiber has been achieved. Control of the system then passes to step 120 in which the cavity heating subroutine is initiated. In this subroutine, the cavity is brought to and held at a predetermined temperature using the following steps:

heat cavity with forced air at predetermined temperature;
measure temperature in cavity;
compare measured temperature to predetermined temperature;

if temperature in cavity is less than predetermined temperature increase temperature of heated forced air;

if temperature in cavity is greater than predetermined temperature, decrease temperature of heated air;

if temperature in cavity is equal to predetermined temperature hold temperature of forced air constant;

return to immediately preceding "measure temperature" step.

When the cavity heating subroutine has achieved the predetermined temperature, the system control passes to step 130 wherein the elongation of the fiber is calculated in percent elongation and stored. Percent elongation is calculated by comparing the fiber length at zero load to the fiber length at the specified load. Fiber length is determined based on the position of the forcer.

When the fiber elongation has been determined and stored, the system control passes to step 140. In step 140 the constant load subroutine and heating subroutine are continued for a predetermined time period.

Upon completion of the predetermined time period as determined by the control system, the system control passes to step 150 wherein the fiber elongation is once again calculated. It will be apparent that during the previous step 140 the length of the fiber can change slightly while the fiber is maintained at a constant temperature and under a constant load. Thus, while the constant load subroutine is continued in step 140, the position of the forcer is periodically adjusted at, for example, about 20 times per second, to maintain the load as sensed by the load cell at the predetermined constant value.

Following step 150, control of the system passes to step 160 wherein the fiber is subjected to a zero load subroutine. In this subroutine, the position of the forcer is slowly adjusted to achieve a zero load on the fiber as follows:

move forcer one position to the right;
sense load reading from load cell;
if reading is greater than zero, return to "move forcer" step;
if reading is equal to zero, return to "sense load reading" step.

When the system has achieved a zero load on the fiber, control is passed to step 170. In step 170, the zero load subroutine and the heat cavity subroutine are continued for a predetermined period of time. Following the predetermined period of time, control of the system passes to step 180.

In step 180, the fiber elongation, based on initial fiber length, is calculated in the manner explained previously. It will be recognized that during the predetermined period of step 170, the fiber length may have decreased slightly as the fiber is maintained under a zero load for the predetermined time period.

Control of the system is next passed to step 190 wherein the constant load subroutine, explained previously, is initiated using a greater predetermined load value than in step 110. In step 190, the constant load subroutine is continued until the system achieves the predetermined load on the fiber according to the predetermined instructions. Thereafter, control of the system is passed to step 200.

In step 200, the system initiates a cooling subroutine to achieve a predetermined cooler temperature in the cavity. The cooling subroutine is comparable to the heating subroutine described previously in connection with step 120; however, the forced air cooling system is used to cool the cavity instead of the forced air heating system used in step 120. When the forced cool air has achieved the predetermined cooler temperature in the cavity, control of the system is passed to step 210.

In step 210, the constant load subroutine and the cooling subroutine are continued for a predetermined period of time. Thereafter, control of the system is passed to step 220.

In step 220, the system initiates the zero load subroutine as explained in connection with step 160. When zero load has been achieved on the fiber, control of the system is passed to step 230.

In step 230, the fiber elongation is calculated, based on initial fiber length as explained in connection with step 130. When the elongation of the fiber has been calculated, control of the system passes to step 240 wherein a written report is generated for the completed test. The written report may include reported values and/or data presented graphically in the form of plotted curves and the like as will be apparent to the skilled artisan.

It will be apparent that stress/strain curves can be generated for various fibers in a similar manner to that discussed above. Following initiation of the system, the linear step motor is moved to the left at the rate specified by the testing protocol. The controller continuously samples the force signals received from load cell 32 and position signals from the forcer to obtain a substantially continuous stress/strain curve information which can be displayed graphically following the test.

The system can also provide data as to, for example, elongation at specified load. Moreover the system can automatically perform the complex work loss test described in U.S. Pat. No. 4,101,525 to Davis et al. without requiring operator input and potential operator error.

The invention has been described in considerable detail with reference to its preferred embodiments. However, variations and modifications can be made with in the spirit and scope of the invention as described in the foregoing specification and defined in the appended claims.

What is claimed is:

1. A fiber testing apparatus comprising:
   a linear step motor including a forcer arranged for controlled linear movement along a stationary platen;
   a first fiber gripping means coupled to said forcer and arranged for linear motion along a predetermined linear path in correspondence with the linear motion of the forcer;
   a second fiber gripping means spaced from said first fiber gripping means and positioned in linear relationship with said predetermined linear path of said first fiber gripping means;
   force measuring means coupled to said second fiber gripping means for measuring force applied to said second fiber gripping means; and
   control means connected to said linear step motor for controlling the linear motion of said forcer, said control means also receiving position signals from said forcer and being connected to said force measuring means for receiving signals from said force measuring means.

2. The fiber testing apparatus defined in claim 1 wherein said force measuring means comprises a load cell.

3. The fiber testing apparatus defined in claim 1 additionally comprising a chamber arranged for containment of said first and said second fiber gripping means whereby a fiber test specimen held by said first and second fiber gripping means can be maintained within the interior of said chamber during testing of the fiber specimen.

4. The fiber testing apparatus defined in claim 3 additionally comprising a heating means for heating the interior of said chamber and a cooling means for cooling said chamber, said heating means and said cooling the interior of means being connected to said control means whereby said heating means and said cooling means are operable in response to signals from said control means.

5. The fiber testing apparatus defined in claim 4 wherein said heating means comprises a means for supplying a forced stream of heated air to said chamber and wherein said cooling means comprises a means for supplying a forced stream of cooled air to said chamber.

6. The fiber testing apparatus defined in claim 5 wherein said chamber comprises a layer of insulating material disposed on the walls thereof so that said fiber test specimen and said first and second fiber gripping means are contained within an insulated thermal environment.

7. The fiber testing apparatus defined in claim 1 wherein said control means comprises a microcomputer.

8. The apparatus of claim 7 additionally comprising a display means connected to said control means.

9. The fiber testing apparatus defined in claim 8 wherein said display means comprises a means for generating a written display.

10. A fiber testing apparatus comprising:
a motor means;
first fiber gripping means coupled to said motor means and arranged for linear motion along a predetermined linear path in response to motion from said motor means;
second fiber gripping means spaced from and positioned in linear relation to said predetermined path of said first fiber gripping means;
force measuring means coupled to said second fiber gripping means for measuring force applied to said second fiber gripping means;
chamber means arranged for containment of said first and said second fiber gripping means in the interior thereof;
heating means arranged for heating the interior of said chamber means;
cooling means arranged for cooling the interior of said chamber means;
temperature sensor means positioned in the interior of said chamber means; and
control means connected to said motor means, said force measuring means, said heating means, said cooling means and said temperature sensor means for controlling thermomechanical testing of a fiber test specimen gripped between said first fiber gripping means and said second fiber gripping means and maintained within the interior of said chamber means.

11. The fiber testing apparatus defined in claim 10 wherein said control means comprises a microcomputer.

12. The fiber testing apparatus defined in claim 11 wherein said motor means comprises a linear step motor including a forcer arranged for controlled linear movement on a stationary platen, said forcer being coupled to said first fiber gripping means so that said first fiber gripping means is moved by said forcer in correspondence with the linear motion of said forcer.

13. The fiber testing apparatus defined in claim 12 wherein said force measuring means comprises a load cell.

14. The fiber testing apparatus defined in claim 13 wherein said heating means comprises a means for supplying a stream of heated forced air to the interior of said chamber means.

15. The fiber testing apparatus defined in claim 14 wherein said cooling means comprises a means for supplying a stream of cooled forced air to the interior of said chamber means.

16. The fiber testing apparatus defined in claim 15 wherein said chamber means comprises a thermal insulation means for maintaining said first fiber gripping means, said second gripping means and said fiber test specimen in a substantially thermally isolated environment.

17. The fiber testing apparatus defined in claim 16 wherein said control means comprises a set of predetermined stored instructions for conducting a standard simulated cure postcure inflation test protocol on said fiber test specimen.

18. The fiber testing apparatus defined in claim 16 additionally comprising a display means connected to said control means for displaying the results of thermomechanical tests conducted on a fiber test specimen.

19. The fiber testing apparatus defined in claim 18 wherein said display means is adapted for providing said display in written form.

20. The fiber testing apparatus defined in claim 16 wherein said control means is adapted to receive position signals from said linear step motor.

* * * * *